United States Patent [19]

Jette

[11] Patent Number: 4,570,074
[45] Date of Patent: Feb. 11, 1986

[54] FLYING SPOT SCANNER SYSTEM
[75] Inventor: Paul Jette, Bethel, Conn.
[73] Assignee: Q-Val Incorporated, Fairfield, Conn.
[21] Appl. No.: 427,620
[22] Filed: Sep. 29, 1982
[51] Int. Cl.$^4$ .............................................. G01H 21/88
[52] U.S. Cl. .................................. 250/563; 250/572; 356/431
[58] Field of Search ............... 250/548, 559, 562, 563, 250/571, 572, 578; 356/237, 430, 431

[56] References Cited
U.S. PATENT DOCUMENTS

| | | | |
|---|---|---|---|
| 3,210,546 | 10/1965 | Perron | 250/563 |
| 3,729,619 | 4/1973 | Laycak et al. | 250/562 |
| 4,013,367 | 3/1977 | Nagao et al. | 250/572 |
| 4,110,047 | 8/1978 | Takahashi | 250/572 |
| 4,398,825 | 8/1983 | Lewis | 356/237 |
| 4,431,309 | 2/1984 | Sick et al. | 250/572 |

Primary Examiner—David C. Nelms
Assistant Examiner—J. Gatto
Attorney, Agent, or Firm—Robert H. Ware; Melvin I. Stoltz; Alfred A. Fressola

[57] ABSTRACT

A flying spot scanner system uses a beam splitting mirror to produce adjacent flying spot images on a material to be analyzed, typically a moving web. The images from the flying spots are split by this beam mirror and sensed by separate photodetectors. The outputs from the photodetectors are algebraically combined on a real time basis, the resultant output signal indicative of web conditions, such as web edges, dirt spots, streaks, scratches and holes. The algebraic output signal amplitude is immune from rapid changes in the web illumination such as caused by changes in external ambient light levels. This signal is also highly immune to variations in the illumination level of the web along the path of the flying spots. The algebraic output signal, by not utilizing differentiation of the received information, has an amplitude independent of the flying spot speeds. The shape of the flying spots can be varied to enhance detection of particular types of defects.

30 Claims, 28 Drawing Figures

FLYING SPOT SCANNER SYSTEM

TECHNICAL FIELD

The present invention relates to scanning apparatus typically used to analyze moving webs, including paper, plastic film, metal sheet, or any other sheet-like material made on a continuous basis. The invention is particularly directed to the manner in which information obtained from the moving web can be used to detect defects in the web including holes, streaks, dirt and scratches.

BACKGROUND ART

There are a number of techniques for examining moving webs which are commonly found in production processes in the paper industry, plastic industry, and other areas in which inspection across the entire width of the moving web to identify defects such as holes, wrinkles, streaks, and dirt are necessary with the web moving at speeds of up to approximately 5000 feet per minute (1,524 meters per minute). Thus the current technology employs such devices as slit scanners, multi-head fixed field detectors, and flying spot scanners. The present invention is directed to the latter type of web defect analyzer and is particularly directed to the method of obtaining flying spot information and using that information to determine the characteristics of the moving web.

Representative of current flying spot web analyzing apparatus is U.S. Pat. No. 4,160,913, Brenholdt. This system, as shown in its FIG. 1, uses a source of illumination 17 (or line source 16 in combination with half-silver mirror 18) to illuminate a web 13 moving in a direction perpendicular to the scan path of flying spot 28. The flying spot is generated by oscillation of mirror 20 with the image of the flying spot passed through lens 19, a mask 24, filter 26, and photodetector 27. The amplitude of the signal is produced by the photodetector is thus a function of the reflected light, ambient light and associated electrical noise. All this information from the photodetector is amplified by pre-amplifier 32 (see FIG. 4 thereof) and differentiated by differentiator 36. A controlled gain amplifier 37 amplifies the output of the differentiator 36, the gain of the amplifier controlled by an automatic gain control (AGC) circuit 39. This output signal is then transferred to an active low pass filter 38, amplified again by amplifier 53 (see FIG. 5 thereof) and then fed to a characterization circuit 50 for determining the type of defect sensed across the moving web.

Differentiator 36 is used to emphasize the changes in the illumination information received from the moving web, in contrast to sensing the amplitude of the signal from the illuminated web. This is done apparently because it would be difficult to use an amplitude threshold as a means of detecting a flaw in the web in view of previously mentioned illumination variations which are not related to such defects. Rather, the differentiator creates a new signal whose amplitude is a function of the rate of change in the received light. The greater the instantaneous rate of increase in the signal, the higher the amplitude of the differentiated output. A rapid decrease in the illumination level of the signal concomitantly results in a very low instantaneously detected output from the differentiator. It is thus seen that the differentiated signal is not soley a function of the amplitude of the input signal but is also a function of its time variation. An abrupt change from a relatively high voltage to a low voltage (as generated by the photodetector 27) momentarily generates a negative value at the differentiated signal output. However, if the input signal stays low, the differentiated signal returns to its nominal value until another change is sensed.

The purpose of the AGC circuit is to set a base level for the rate of change based on the average rate of change across the web. This base level is established by charging a capacitor through an analog switch during the first part of each scan. Throughout the balance of the scan, the level established is subtracted from the differentiated signal, the resulting signal is then low pass filtered and transferred to the characterization circuit.

If the web has a hole, it is perceived by the Brenholdt disclosure as being darker than the surrounding web whereas a wrinkle is perceived as being a region of relatively greater brightness. As shown in FIG. 7 of Brenholdt, the signal from the detector shows holes as a slight positive anomaly and wrinkles as a negative anomaly. Waveform B of FIG. 7 shows that after differentiation, a small hole generates a positive pulse immediately followed by a negative going pulse whereas a wrinkle generates a negative pulse followed by a positive pulse.

The characterization circuit in Brenholdt seeks to distinguish such events (including determination of edges) and indicate their occurrence to the outside world. The system uses four signal events; namely, a large isolated negative pulse indicating the leading edge of the web; a smaller negative pulse immediately followed by a similarly sized positive pulse indicating a hole; a small positive pulse immediately followed by a similarly sized negative pulse indicating a wrinkle or streak; and a large isolated positive pulse indicating the trailing or far end of the web. The characterization circuit must therefore be able to detect such pulses and their time relationship with respect to each other.

In summary, the Brenholdt disclosure specifies a means by which a differentiated signal from a single sensor radiated by a flying spot scanning apparatus can be used to detect wrinkles, holes and edges associated with a moving web and to distinguish them by the order of the positive and negative transitions of the differentiated sensed signal. However, due to the fact that a differentiated signal is used, inherent noise problems associated with differentiation are present. Such problems include rapid changes in the overall illumination of the flying spot such as caused by changes in external illumination of the web in the area of the flying spot. Thus, for instance, if light from a skylight suddenly appeared on the web, this would generate a change in the illumination level. A change could also be caused by momentary blockage of an extraneous light source such as would result from a moving vehicle.

The present invention uses a different technique for producing a signal indicative of defects in a moving web by generating two flying spots adjacent to one another which scan the moving web. Instead of differentiating a single flying spot signal, the present invention produces an algebraically combined output signal from the two flying spots to provide web defect information. The present invention can alternatively be thought of as generating a single flying spot which is split into two adjacent halves. Regardless of how it is conceptually considered, the significance of the two simultaneous signals is that the system can simultaneously compare two adjacent points on the web to determine if the same amount of light is being respectively received. If the illumination is different for the two areas, then a defect of some sort (or edge) is being detected; the two flying spots in essence straddling the defect (or edge). A particular advantage of this arrangement is that abrupt changes in the level of ambient illumination do not affect the sensors differently. Thus an algebraic combination of the two signals is not affected.

In the present system comparison of the light reflected simultaneously from two adjacent flying spots on the web is sensed by spatially displaced photodetectors. The amplified signals from these photodetectors are combined in a particular manner to enable detection of relatively small differences in their respective illumination. Thus the present invention performs defect signal generation by operating in the space domain while the Brenholdt reference, by time differentiation of a single signal operates in the time domain.

Although U.S. Pat. No. 3,322,024, Preston, discloses an optical technique for the inspection of a transparent object for defects which uses two illumination sources, the apparatus operates in a manner completely unlike the present invention. In particular, the apparatus is for observing defects in a transparent medium such as glass, and it employs two light sources in order to develop illumination of alternate light and dark bands if a defect known as "wave" is present in the sheet glass. It does not use a flying spot technique nor two or more flying spot signals which are statially adjacent to each other with their signals algebraically combined to enable defect discrimination.

A number of other prior art references are directed light scanning apparatus such as set forth in Group I below

| | GROUP I | |
|---|---|---|
| Inventor | U.S. Pat. No. | Issue Date |
| Harries | 2,993,403 | 1961 |
| Greunke | 3,060,319 | 1962 |
| Poor | 3,087,373 | 1963 |
| Gaffard | 3,338,130 | 1967 |
| Dostal | 3,532,408 | 1970 |
| Brichard | 3,543,033 | 1970 |
| Corker | 3,642,344 | 1972 |

The references in Group I all describe optical scanning systems in which scanning is achieved by oscillating a mirror which, in each case, is supported by a torsion bar assembly. Although the present invention uses a scanning mirror supported by a taut band (which is similar to a torsion bar), none of these references disclose or suggest a scanning system having two flying spots adjacent to one another for scanning an output signal by the algebraic comparison of signals as received by separate photodetectors. They also neither disclose nor suggest adjusting the shape of the flying spot images in order to facilitate the detection of particular types of defects.

The references in Group II below show various types of scanning apparatus which, though relevant as showing the state of the art, neither disclose nor suggest the present invention including use of multiple flying spots for scanning the moving web and separate photodetectors each individually associated with one of the flying spots with the detection of defects obtained through comparison of the flying spot images rather than through use of a single flying spot image.

| | GROUP II | |
|---|---|---|
| Inventor | U.S. Pat. No. | Issue Date |
| Jorgensen | 3,410,643 | 1968 |
| McKown | 3,516,743 | 1970 |
| Kurotschka | 3,589,792 | 1971 |
| Bhullar et al | 3,646,353 | 1972 |
| West et al | 3,686,008 | 1970 |
| Rosin | 3,687,025 | 1972 |
| Kaneko et al | 3,774,041 | 1973 |
| Bertoya et al | 3,779,649 | 1973 |
| Shaw | 3,871,773 | 1975 |
| Buckson | 3,970,857 | 1976 |
| Reinke | 4,003,626 | 1977 |
| Craig | 4,038,554 | 1977 |

Another reference, U.S. Pat. No. 3,797,943, Naoao et al discloses a surface inspecting apparatus which incorporates a slit plate having a plurality of slits of different shapes which determine the field of vision for the object to be inspected. Although the apparatus uses a plurality of photoelectric conversion devices (see FIG. 1 thereof) each photodetector is associated with a different slit shaped in slit plate 7. It is used for discriminating particular types of defects since a defect which most closely fills a particular slit shape produces the greatest signal (see FIG. 6 thereof). This reference therefore does not disclose or suggest the use of a multiple flying spots with separate detection of each flying spot, nor of the comparison of these signals on an instantaneous basis in order to determine not only when a defect occurs but the type of defect through the relationship of the signals to one another.

Therefore, none of the prior art references cited are believed to disclose or suggest the present flying spot scanner system.

DISCLOSURE OF THE INVENTION

The present invention is a flying spot scanner system especially for use as part of a moving sheet material (called web herein) defect analyzer commonly found in the manufacture of paper, plastics, glass and various metals. Defects in such webs include holes, dirt, streaks, and scratches. Strains, flaws, cracks and deformations are also commonly encountered in the manufacture of sheet metals. It is highly advantageous therefore to detect such defects as soon as possible in order that corrective action may be taken. Due to the fact that many sheet materials are produced at high speeds (up to 5000 feet per minute (1,524 meters per minute) human visual inspection is at best faulty and automatic mechanical devices highly desirable. As set forth in the background section, a number of devices exist in the art for conducting various types of inspection techniques on moving webs.

The present invention provides a new technique which uses flying spot technology and enhances it through use of a multiple flying spot mechanism. In particular, the present invention inspects a web illuminated from a light source from either below or above the web. The inspection is performed by a pair of flying spots imaged on the web by a split beam mirror in association with a lens system. The flying spots scan the moving web in a direction perpendicular to the web or machine direction by oscillation of a scanning mirror. The received light (the imaged flying spots) reflected by the oscillating mirror is presented to the split beam mirror which separates the flying spot images, each flying spot image separately detected by an individual photodetector. The signals from the photodetectors are simultaneously compared with detection of a defect performed as a result of the variation in the light level associated between the two images. Thus, the present invention performs defect identification through operation in the space domain rather than in the time domain.

Since the present invention operates in the space domain, time variations in the overall illumination level of the web do not adversely affect operation of the device. Thus a change in illumination level of the web such as associated by an extraneous exterior light source impinging on the web, would equally affect both flying spot images and thus the comparison of the images is not affected. This is similarly true where the illumination level varies across the width of the web along the path of the flying spots such as might result when the illumination source, typically a lightbox, has one or more defective bulbs. Such cross web source light fluctuations can also result from the normal cyclical variations of the illumination as a result of alternating current electrical sources for energizing the light bulbs of the illumination source. This is especially prevalent when gas discharge lights, such as fluorescent bulbs, provide the illumination. In either case, the non-uniform illumination of the web is again substantially equally detected simultaneously by the individual flying spots and thus the comparison of their signals is not adversely affected.

Consequently, in order to detect a defect and to identify types of defects, it is only necessary to perform analysis of the algebraically combined output signal developed from the two detectors. In a typical situation where a small hole is encountered by the flying spots and where the web is illuminated from below, the received signal of the leading flying spot first increases due to light passing through the hole while the trailing flying spot at first does not "see" the hole and thus maintains its previous illumination level. The ratio of the two signals when plotted as the flying spots traverse the hole thus instantaneously shows an increased level as the hole is first detected (that is the signal from the leading flying spot is greater than that of the trailing flying spot), and a decreased level as the trailing flying spot traverses the hole (the signal from the trailing flying spot is greater than the leading flying spot). A simple amplitude threshold device can then be employed to detect such a defect and the overall magnitude of this algebraic signal is further indicative of the type of defect. In the given example with a small hole as the defect, the integral of the ratioed signal is greater than the normal signal and thus detection of a positive going integral signal is indicative of a small hole.

Conversely, if a small dark spot is encountered (such as associated with a spot of dirt on the moving web), the leading flying spot first has a reduced signal with respect to the trailing flying spot and thus the comparison of these two signals first generate a lower than normal signal followed by a signal that is greater than normal as the trailing flying spot detects the dark spot. In such a case, an integral of the algebraic signal has an overall value always less than the normal web surface signal and detection thereof is indicative of a small dark defect. Thus, overall magnitude levels can be used for detection of defects and identification of the type of defects encountered.

In further amplification of this observation, if a streak is encountered having a direction in the machine direction, the leading flying spot signal is first reduced with respect to the trailing flying spot signal, and vice versa as the trailing flying spot detects the streak. Since the streak is in the direction of the moving web, the amplitude of this signal is greater than that associated with a small hole provided the flying spots have a sufficiently large machine direction footprint. Thus, the amplitude of the algebraic signal is greater than that associated with detection of either a small hole or a small dark spot. Furthermore, the integral value of the algebraic signal has a greater negative going size than that associated with a small dark spot. This result allows not only streak defect detection but streak identification. Other procedures can of course be used to identify the type of defective including the reoccurrence of a defect during consecutive scans of the web.

To enhance detection of various types of defects, the shape of the flying spots can be altered. Thus, triangularly-shaped flying spots provide gradual increase of an algebraically compared signal for a streak as the streak enters the leading flying spot. An abrupt change is sensed as the streak leaves the leading flying spot and enters the trailing flying spot. A gradual decrease is sensed as the streak exits the trailing flying spot.

Small holes however do not exhibit a greatly more significant transition while leaving the leading flying spot and entering the trailing spot than they do when entering the leading flying spot or exiting the trailing flying spot. This mirror geometry therefore enhances streak detection; whereas discrete defect detection sensitivity is dependent on what portion of the footprint is used. A long machine direction flying spot footprint is advantageous for detecting machine direction defects such as streaks or scratches due to the large signal associated with such defects. It also provides a uniform detection of holes and dark spots. Thus the present invention provides a new mechanism by which web defects can be detected.

OBJECTS OF THE INVENTION

Therefore it is a principal object of the present invention to provide a flying spot scanner system for use with a defect analyzer, the scanner using multiple adjacent flying spots for use in generating a signal for detection and identification of web defects.

It is another object of the present invention to provide a flying spot scanner of the above description in which individual photodetectors are associated with each flying spot and in which the signal for detection and characterization of the defect is generated by simultaneously algebraically comparing the signals from the separate photodetectors.

Another object of the present invention is to provide a flying spot scanner of the above description in which a beam splitting mirror generates triangularly shaped flying spot footprints on the web so as to improve the device's sensitivity for detecting streaks.

A still further object of the present invention is to provide a flying spot scanner of the above description in which the beam splitting mirror generates elongated rectangular footprints on the moving web, the rectangular footprint having its elongated axis parallel to the machine direction of the web so as to provide uniform detection of holes and dark spots while maintaining good streak detection.

Another object of the present invention is to provide a flying spot scanner in which an algebraically compared output of two flying spot signals is processed to obtain an integral value of this output.

An additional object of the present invention is to provide a flying spot scanner wherein the algebraic comparison of the flying spot signal is particularly sensitive to detecting relatively small differences in value between the two signals as compared to their absolute magnitudes.

Another object of the present invention is to provide a flying spot scanner using feedback circuitry to balance the amplified flying spot signals to each other during a portion of each scan so as to increase the precision of the system to detect defects.

Other objects of the present invention will in part be obvious and will in part appear hereinafter.

BRIEF DESCRIPTION OF THE DRAWINGS

For a fuller understanding of the nature and objects of the present invention, reference should be made to the following detailed description taken in connection with the accompanying drawings in which:

FIG. 7C is a diagram showing how FIGS. 7A and 7B are put together to form FIG. 7.

BEST MODE FOR CARRYING OUT THE INVENTION

Figure 1:
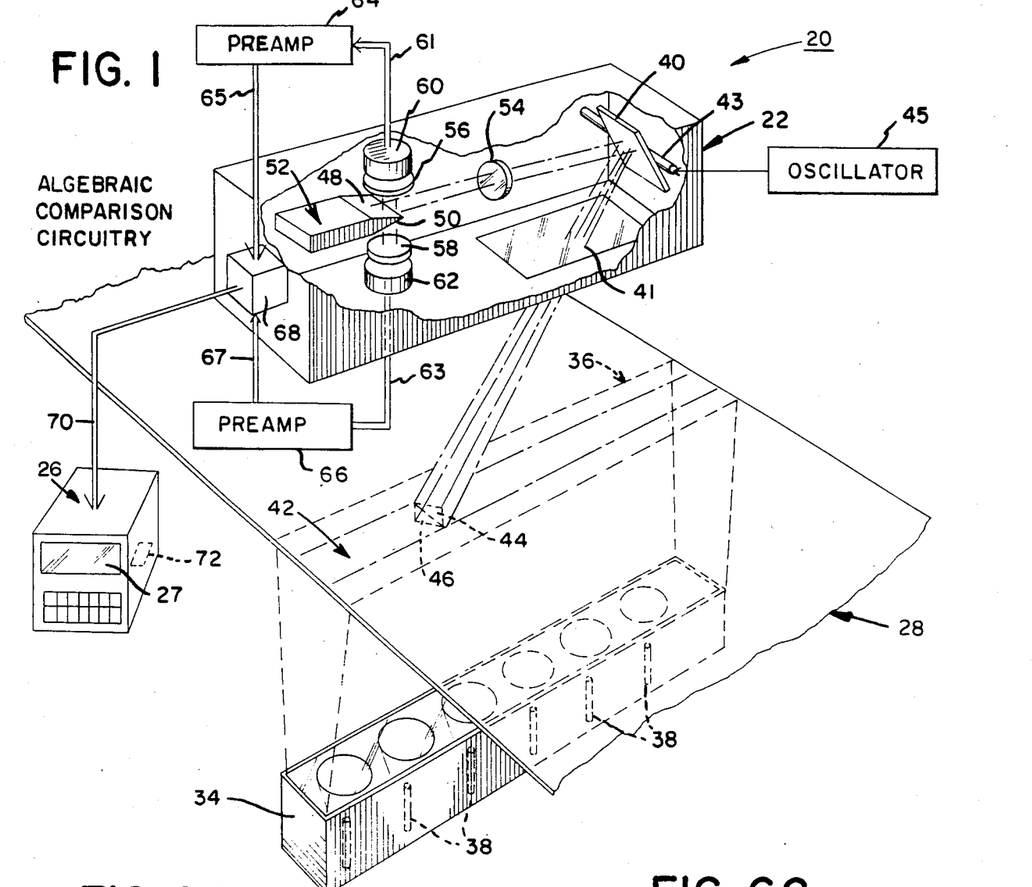
FIG. 1 is a diagrammatic perspective view of a flying spot scanner system according to the present invention, mounted for operation to scan a moving web, illustrating the illumination source, the illumination area on the moving web, the path of the flying spots across the moving web and the beam splitting and detection portions of the scanner system as well as showing in diagrammatic form the additional circuitry and console which can be associated with the present invention.
Figures 2, 3:
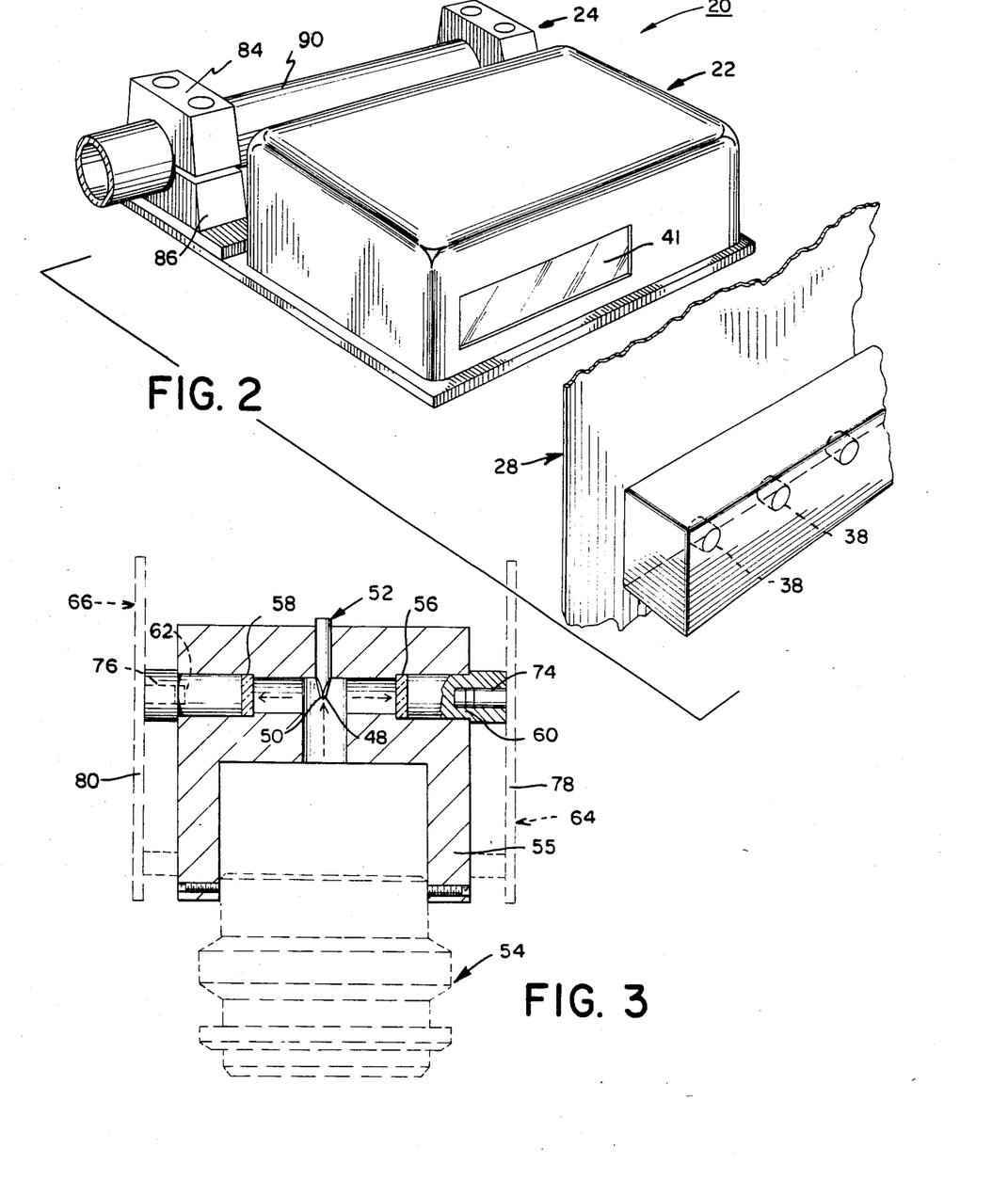
FIG. 2 a perspective view of the flying spot generator housing for the scanning mirror, the beam splitting mirror pre-amplifier and algebraic comparison circuitry, and showing the window associated with the housing for scanning a moving web with a diagrammatic representation of the web illumination area and web direction.
FIG. 3 a cross-sectional top view of the primary lens system and beam splitting mirror mounting block, showing in phantom the placement of the primary objective within the housing, and also showing the beam splitting mirror, the secondary lenses, the photodiodes, and the pre-amplifier printed circuit boards associated with each photodiode.
Figure 4A:
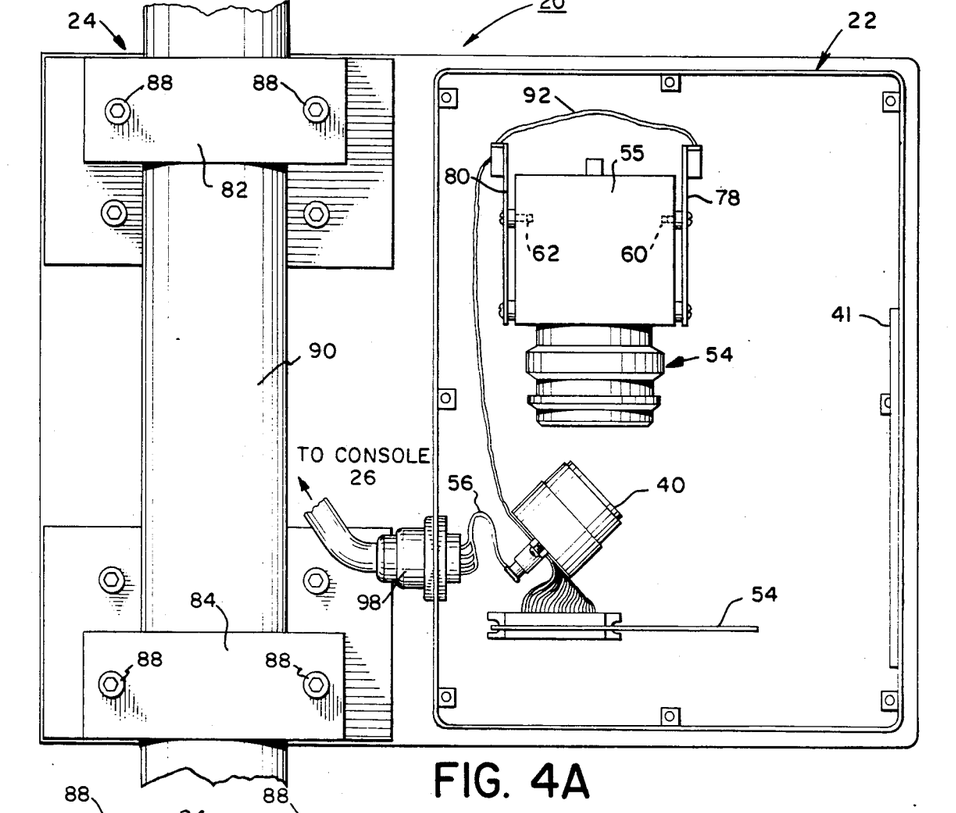
FIG. 4A is a plan view of the scanner housing and mounting hardware shown in FIG. 2 illustrating the interior of the scanner housing with the cover of the housing removed so as to show the beam splitting mirror and primary lens system housing, the housing for the scanning mirror and the internal electronics associated therewith.
Figure 4B:
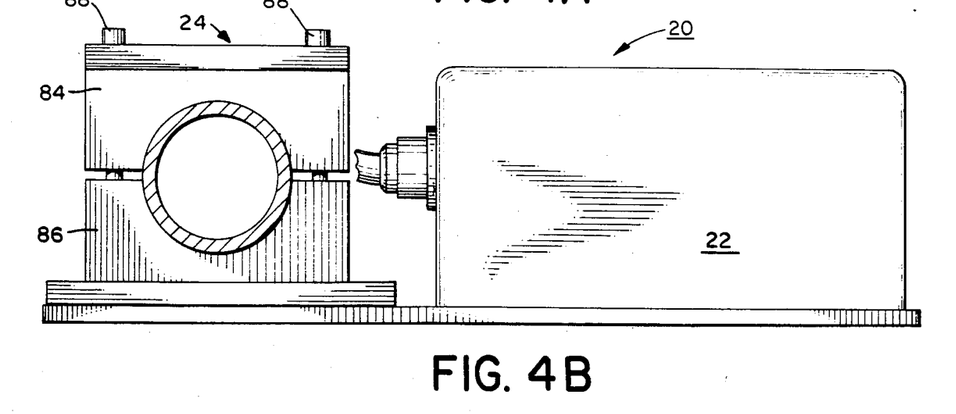
FIG. 4B is a side elevational view of the scanner housing and mounting hardware as shown in FIG. 4A with the cover of the scanner housing in place.

As best seen in FIGS. 1, 2, 4A and 4B, a flying spot scanner system 20 comprises a scanner housing 22 within which is mounted a scanning mirror 40, a primary lens 54, a beam splitting mirror 52, secondary lenses 56 and 58 and photodetectors 60 and 62. Light passes into housing 22 through window 41. Outputs 61 and 63 from photodetectors 60 and 62 are amplified by pre-amplifiers 64 and 66. Outputs 65 and 67 from these pre-amplifiers are connected to algebraic comparison circuitry module 68. The algebraically compared output 70 can then be transferred to a console 26 for further processing by circuitry 72. The processed information can be presented to display 27 and/or stored or transferred to other equipment. As shown in FIGS. 2, 4A and 4B, scanner housing 22 can be connected to mounting hardware 24 so as to position scanning mirror 40 in proper alignment with moving web 28.

The flying spot scanner system provides the electrical signals for defect detection and identification of moving web 28. As shown in FIG. 7 these defects typically include holes 30, scratches 31 dirt spots 32 and any other type of defect which has a different optical characteristic than that of the underlying web. The web can be any type of sheet-like material and in particular can include paper and paper-related products thin film plastics, sheet metal and the like. In the embodiment shown in FIG. 1, the flying spot scanner system uses a light box 34 for back-lighting the web along a generally rectangular illumination area 36. The light box can comprise a plurality of light bulbs 38 or any other type of light producing device. Unlike prior art flying spot scanners, the illumination along the illumination area 36 need not be precisely uniform in order for the flying spot scanner system to operate with uniform cross-web sensitivity.

As also seen in FIG. 1, the scanning mirror 40 is mounted on a torsion bar 43 which is driven by oscillator 45 so as to rapidly oscillate back and forth and thus to traverse the illumination area 36 within a scanning area 42.

Figures 5A, 5B, 5C, 7A:
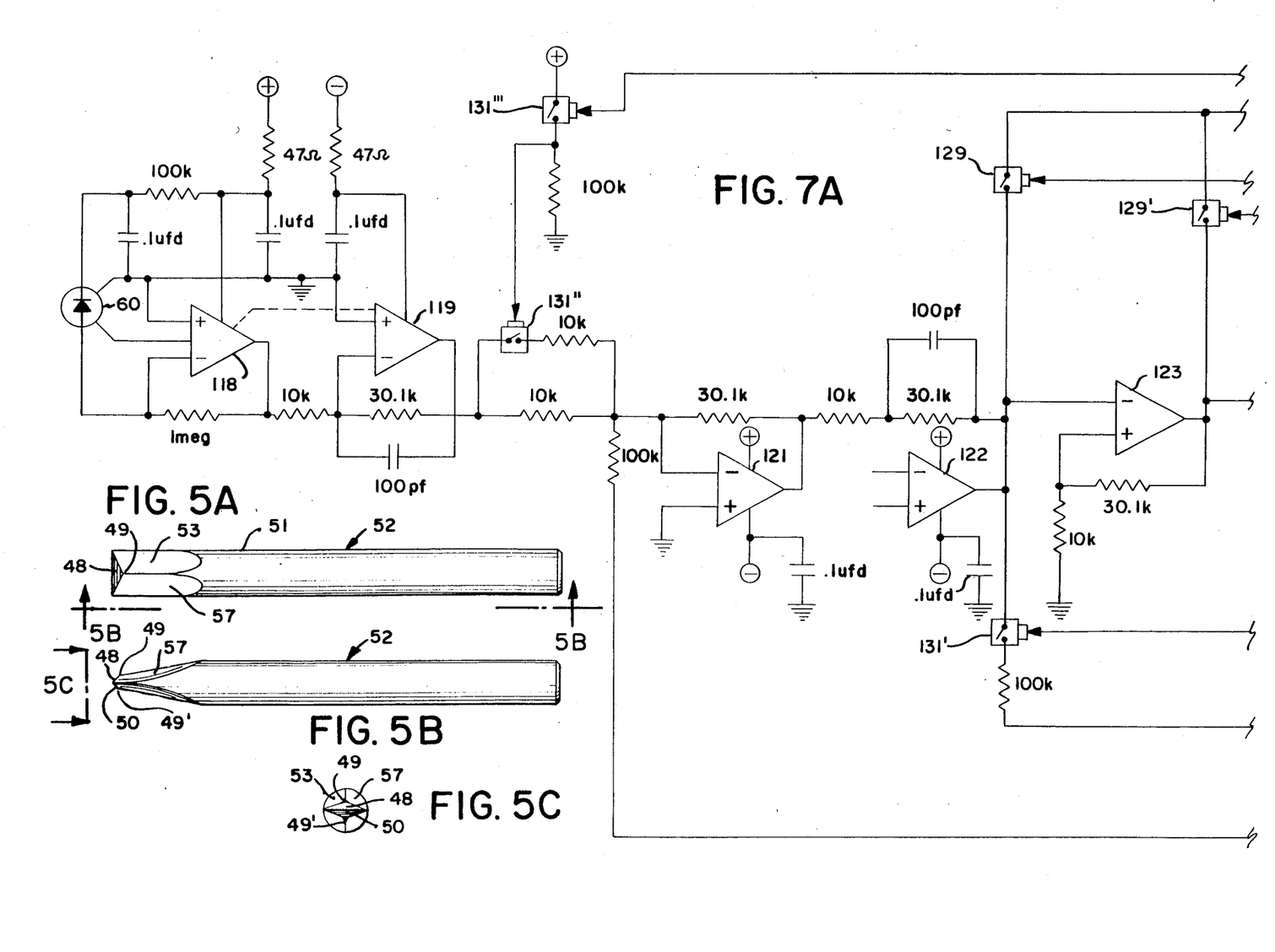
FIG. 5A is an enlarged view of the beam splitting mirror and shaft shown in FIG. 3.
FIG. 5B is a view of the beam splitting mirror and shaft shown in FIG. 5A, taken along line 5B—5B of FIG. 5A.
FIG. 5C is a front view of the beam splitting mirror shown in FIGS. 5A and 5B taken along line 5C—5C of FIG. 5B.
FIG. 7A is a portion of a detailed schematic of the pre-amplifier electronic circuitry associated with the flying spot scanner system.

In the preferred embodiment of the present invention, the scan image upon the web at any particular instant in time comprises two adjacent flying spot footprints 44 and 46 whose shape are determined by the mirrored surfaces 48 and 50 of split beam mirror 52. These flying spot footprints are in fact generated as imaged areas by primary lens 54 whose image is then split by mirrored surfaces 48 and 50 and projected by secondary lenses 56 and 58 onto corresponding photodetectors 60 and 62. As seen in FIGS. 5A-5C the mirrored surface 48 and 50 are located in the extreme end of faces 53 and 57 at one end of shaft 51 mirror 52. The overall length of shaft 51 is 0.875 inch (2.22 cm), with a shaft diameter of 0.0995 inch (0.25 cm) or 0.199 inch (0.51 cm). The mirrored surface subtends an angle of 90 degrees. As shown in FIG. 5C, their upper and lower terminations (between points 49 and 49') equals 0.038 inch (0.09 cm). The embodiment shown in FIG. 5A-5C generates triangularly shaped footprints 44 and 46 such as shown in FIGS. 1 and 8B.

Figure 6A:
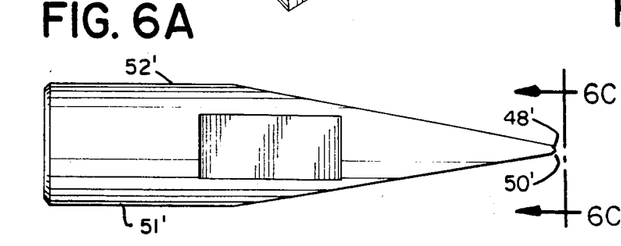
FIG. 6A a side view of a different embodiment of the beam splitting mirror, showing the faces of the beam splitting mirror on edge, the shape producing a generally elongated rectangular footprint on the web to be analyzed.
Figure 6B:
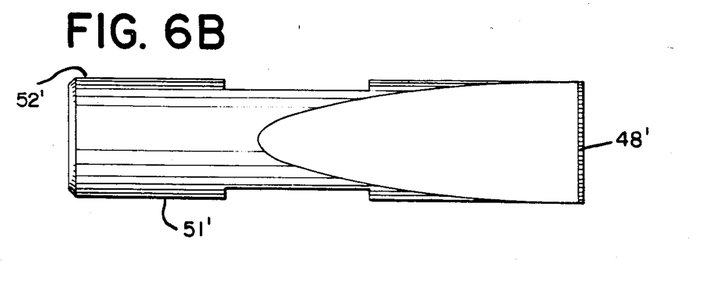
FIG. 6B is a view of the beam splitting mirror shown in FIG. 6A.
Figure 6C:
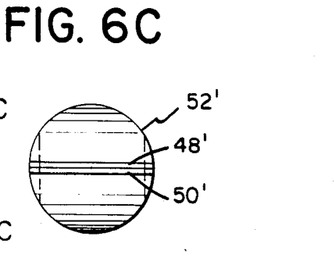
FIG. 6C is a front view of the beams splitting mirror shown in FIGS. 6A and 6B taken along line 6C—6C of FIG. 6A.
Figure 9A:
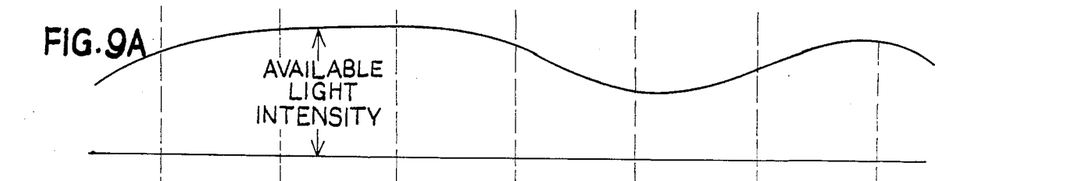
FIGS. 9A–9F are waveforms associated with rectangularly shaped flying spots
Figure 9B:
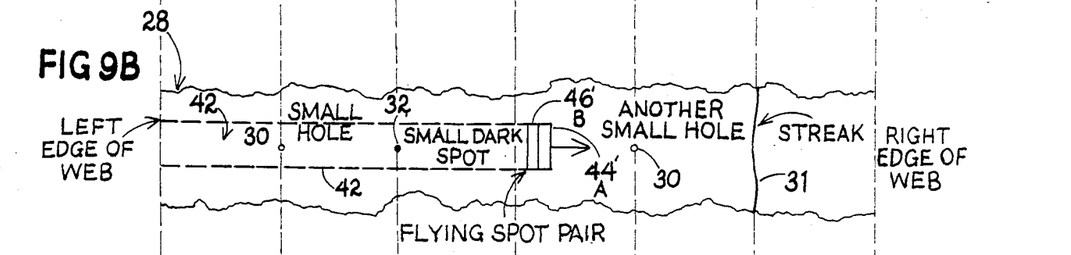
Figure 9C:
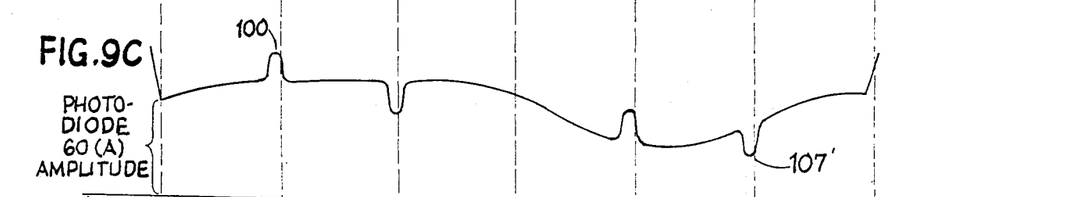
Figure 9D:
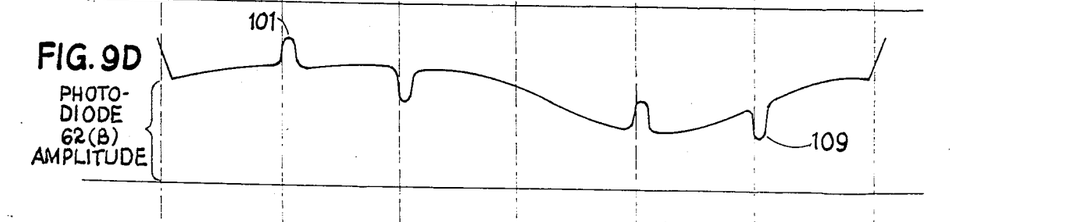

FIGS. 6A-6C illustrate mirrored surfaces 48' and 50' that generate rectangular footprints 44' and 46' as shown in FIG. 9B. Shaft 51' also has a length of 0.875 inch (2.22 cm) and a diameter of 0.199 inch (0.51 cm). Mirrored surfaces 48' and 50' subtend an angle of 90 degree and have a displacement between their upper and lower terminations of 0.01 inch (0.025 cm) (See FIG. 6C). The output from the photodetectors is presented to individual pre-amplifiers 64 and 66 whose outputs are combined via algebraic comparison circuitry 68 so as to produce a composite signal output 70. This algebraically combined output may then be presented to electronic circuitry 72 within control console 26 for processing in order to determine the occurrence and types of defects which may be present on web 28. Such circuitry does not comprise part of the flying spot scanner system.

FIG. 3 illustrates the detailed mechanical configuration of lens 54 in combination with the split beam mirror 52, secondary lenses 56 and 58 and photodetectors 60 and 62. The primary lens 54 may be any standard photographic quality lens such as that manufactured by the Canon Company of Japan. The photodetectors 60 and 62, which in the preferred embodiment are photodiodes, are mounted on respective standoffs 74 and 76 which are mounted on printed circuit boards 78 and 80. Pre-amplifiers 64 and 66 respectively are mounted on these boards.

The internal configuration of the scanner housing 22 is shown in FIG. 4A in conjunction with mounting hardware 24. As seen in FIGS. 2, 4A and 4B, the mounting hardware 24 comprises a pair of circular cross-sectional cut out blocks 82 and 84 which respectively mount onto mating blocks 86 through use of machine screws 88. The split-ring shaped blocks are positioned about a pipe 90 which is firmly attached to the floor or other support within which the scanner system is to be mounted. In this way, the scanner housing can be positioned in the desired orientation to optically traverse the moving web.

FIG. 4A also illustrates the orientation of the scanning mirror 40 with respect to window 41 and primary lens 54 as well as the primary lens housing 55 with respect to printed circuit boards 78 and 80. These printed circuit boards are connected to each other via ribbon cable 92 which transmits both pre-amplified signals 65 and 67 (See FIG. 1) to printed circuit board 94. This circuit board houses the electronic circuitry for the algebraic comparison circuitry 68 (see FIG. 1). Output signal 70 from this circuitry is transferred by a second ribbon cable 96 to a plug 98 for ultimate transfer to console 26.

Operation of the Flying Spot Scanner System

Figure 8A:
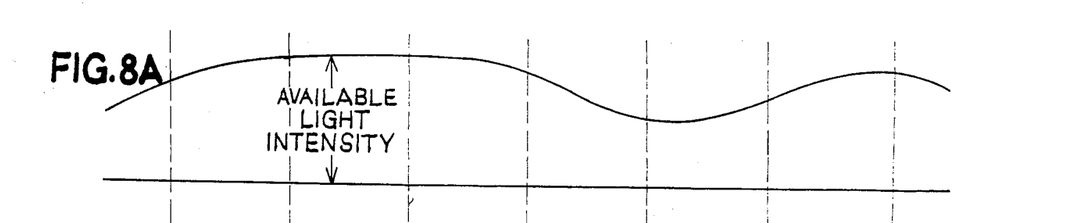
FIGS. 8A–8F are waveforms associated with triangularly shaped flying spots.
Figure 8B:
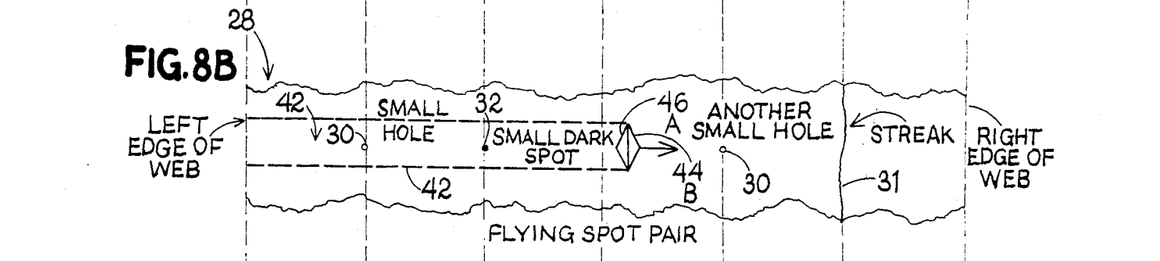

FIGS. 8A-8E illustrate typical waveforms regarding use of the flying spot scanner system. In FIG. 8A, the amplitude of the available light as a function of time is plotted. The horizontal axis for the FIGS. 8C-8F are similarly plotted against time. The variation in available light shown in FIG. 8A could result from external extraneous light falling onto the web. Such light can of course vary in intensity at any given time.

FIG. 8B, shows a typical portion of a web falling within this scan area 42. In the particular example, the flying spot footprints 44 and 46 are of a triangular configuration which correspond to the shape of the split beam mirror surfaces 48 and 50 for one embodiment of the split beam mirror. As shown in FIG. 8B, the region of web 28 within the scan area 42 includes a first small hole 30, a small dark spot 32, a second small hole 30' and a streak 31.

Figure 8C:
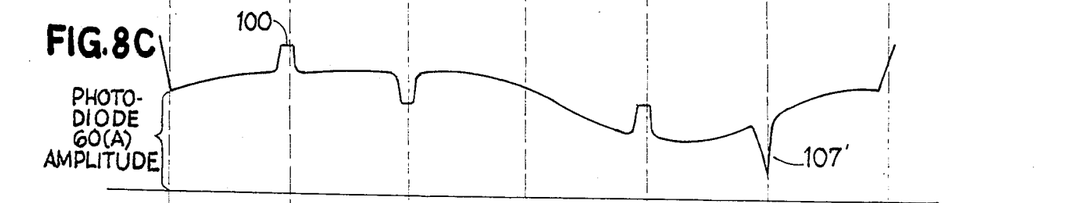
Figure 8D:
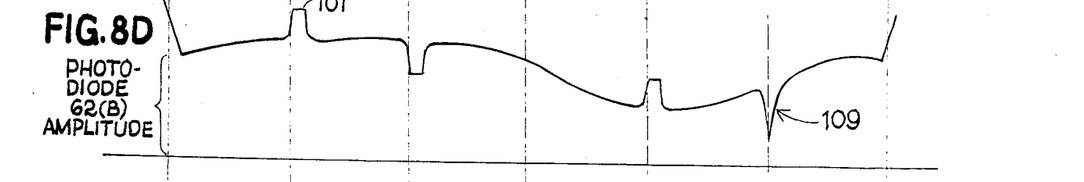

FIGS. 8C and 8D illustrate the outputs 61 and 63 (also labeled "A" and "B" respectively) from photodetectors 60 and 62 (which in the preferred embodiment are photodiodes) as the flying spot traverses the web. Photodiode 60 is associated with leading flying spot 44 while photodiode 62 is associated with trailing flying spot 46. In the example of the first hole 30, flying spot 44 first detects the defect and thus the occurrence of pulse 100 is before the corresponding occurrence of pulse 101 for photodiode 62. It should be noted that for both photodiode amplitudes vary in an overall manner proportional to the available light intensity as shown in FIG. 8A. However, the algebraically combined output of these two signals does not show any appreciable change with respect to variations in the available light intensity. This is seen in FIG. 8D where the output of photodiode 62 subtracted from that of photodiode 60, the resultant divided by the addition of these two output signals.

In the example of small hole 30, because pulse 100 occurs before pulse 101, the numerator of this algebraic comparison is first greater than the normal base line. This result is shown by positive pulse 102 in FIG. 8E. Later, when pulse 101 occurs and pulse 100 has ended, output 70 is less than the base line as shown by negative going pulse 103.

This algebraic comparison output illustrates an important aspect of the present invention, namely that it is extremely insensitive to variations in available light intensity including variations of such intensity at particular locations along the web. The latter condition can result from the burn out of one or more bulbs in the lightbox 34. In the given example shown in FIGS. 1 and 2 where the web is back lighted causing an increase in the amplitude of the sensed photodiode when its corresponding flying spot is over the defect, the nature of the defect can be determined in part by the spatial correspondence of pulses in the algebraic comparison output as well as by its overall magnitude. In the case of the small hole, the leading flying spot increases in amplitude versus the trailing second flying spot and thus their algebraically compared output has a configuration as shown by pulses 102 and 103 in FIG. 8E. A dark spot as shown in FIG. 8B results in a reverse type waveform corresponding to pulses 104 and 105 in FIG. 8E.

Figure 8E:
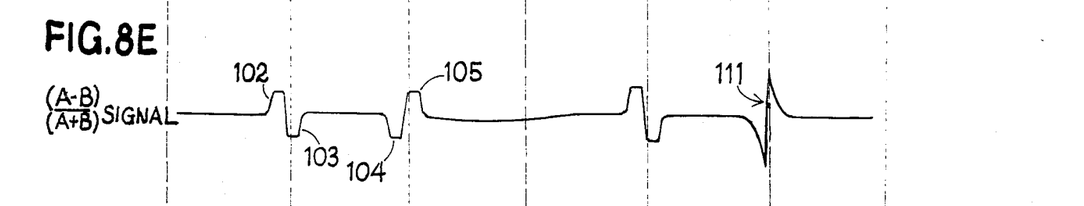

FIG. 8B also shows a streak 31. Photodiode 60 when it encounters the streak generates waveform 107 while photodiode 62 generates a mirror image waveform at a later time as shown by waveform 109. The algebraic comparison of these two waveforms is shown in FIG. 8E by waveform 111 and it is there seen to have a first negative going pulse and later a positive going pulse with amplitudes greater than those of negative and positive going pulses 104 and 105 for the small dark spot. The reason for this is the streak as encountered by the triangularly shaped flying spot 44 first causes a greater reduction of the received light by the first photodetector than that for a dark spot. Consequently, there is a steady reduction in this photodiode's output as the streak is first scanned. A sharp transition occurs as the leading flying spot completes its scan of the streak while the trailing flying spot "sees" a sharp reduction in light as the streak enters its footprint having the longest machine direction length (see waveform 109). The trailing flying spot gradually "sees" less of the streak as it passes over the streak. This accounts for the gradual return of its output signal to the nominal value.

Figure 7E:
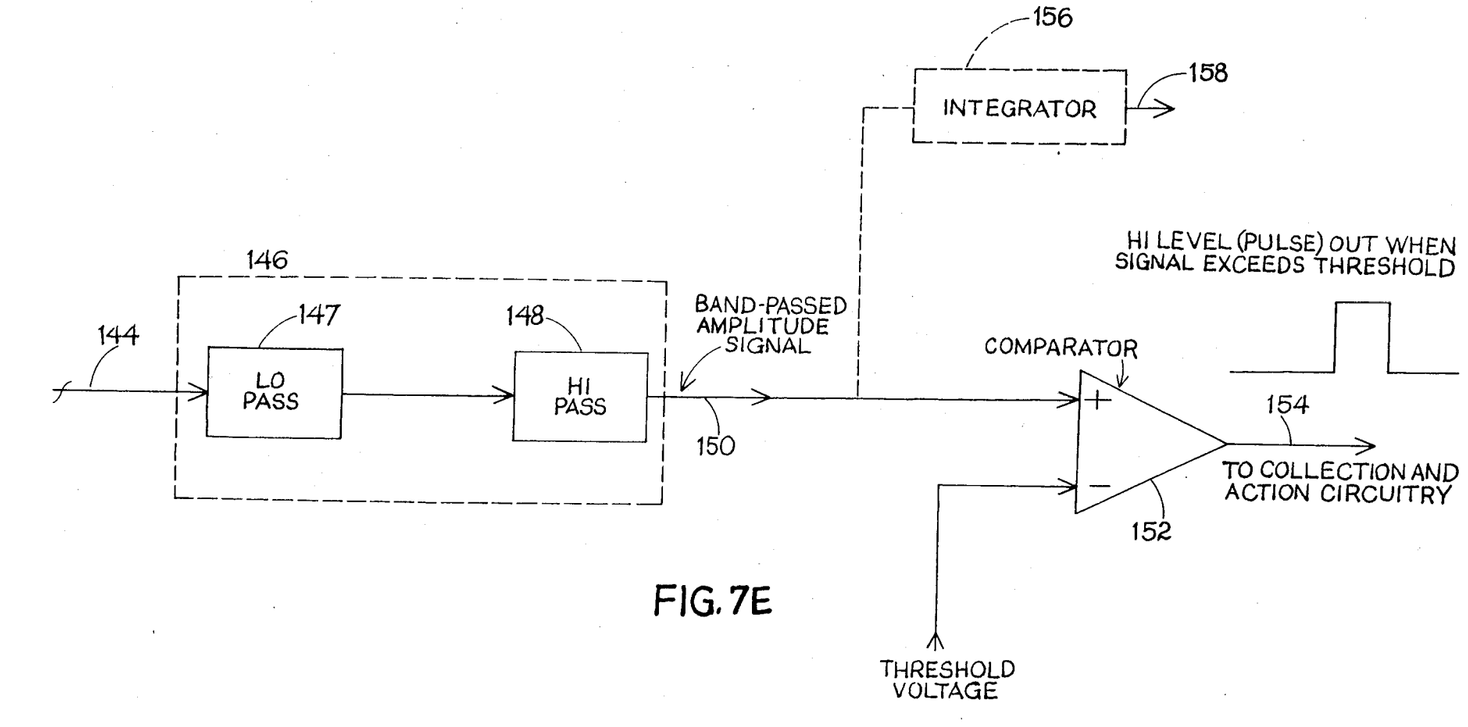
FIG. 7E is a block diagram of a flying spot scanner circuitry which can be used in combination with the present invention to detect and identify web defects.
Figure 8F:
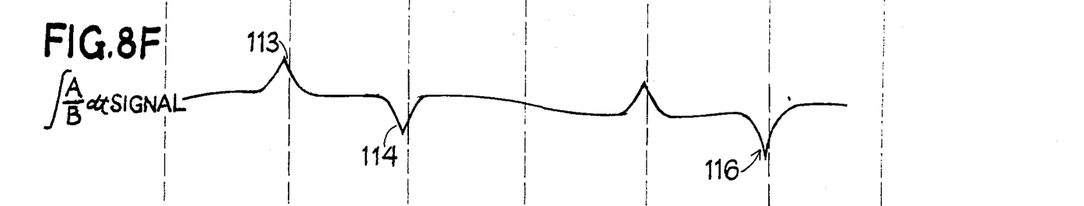

The waveforms for a small hole, a small spot, and streaks as shown in FIG. 8E can be identified by the nature of the waveforms, that is, whether they are first positive going and then negative going as well as their respective amplitudes. This processing can be facilitated by integrating the algebraic comparison signal by an integrator 156 (see FIG. 7E) with the resultant waveforms as shown in FIG. 8F. Thus, a small hole generates a positive going waveform 113 while a small dark spot generates a negative going pulse 114. A streak generates a greater amplitude negative going pulse 116 in comparison to the small dark spot. Such processing of the algebraic comparison signal need not form part of the flying spot scanner system.

Figure 9E:
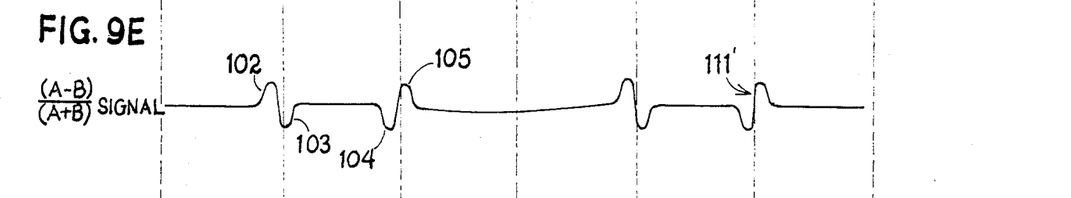
Figure 9F:
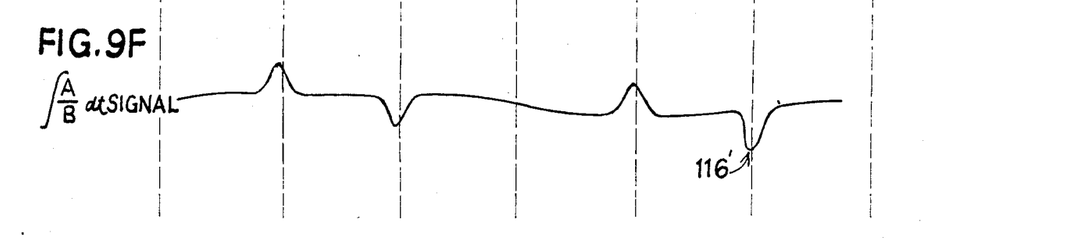

FIGS. 6A, 6B, and 6C illustrate another embodiment of the split beam mirror, where mirrored surfaces 48' and 50' have a rectangular shape. Their footprints are thus rectangular as shown in FIG. 9B. The outputs for the two photodiodes as a small hole or a small dark spot is encountered are similar to yet somewhat rounder versions of, those for the triangularly shaped flying spots since such small defects have a machine direction length relatively small in comparison to the flying spot footprints (see pulses 100', 101', 102', 103', 104' and 105'). However, the streak causes a different type of output as shown by waveform 107' and 109' for the two photodiodes. The more rectangularly shaped pulse is due to the rectangular shape of the flying spots and thus the instant the streak is detected by the first flying spot it "sees" a dramatic reduction in light. This similarly occurs when the streak is detected by the second flying spot 46'. This result is in contrast to the gradual reduction in the sensed light for the triangularly shaped flying spots 44 and 46. The algebraic comparison signal is thus greater as seen in FIG. 9E for waveform 111' as is the resultant integral value as shown by waveform 116' in FIG. 9F.

ELECTRONIC CIRCUITRY

Figure 7B:
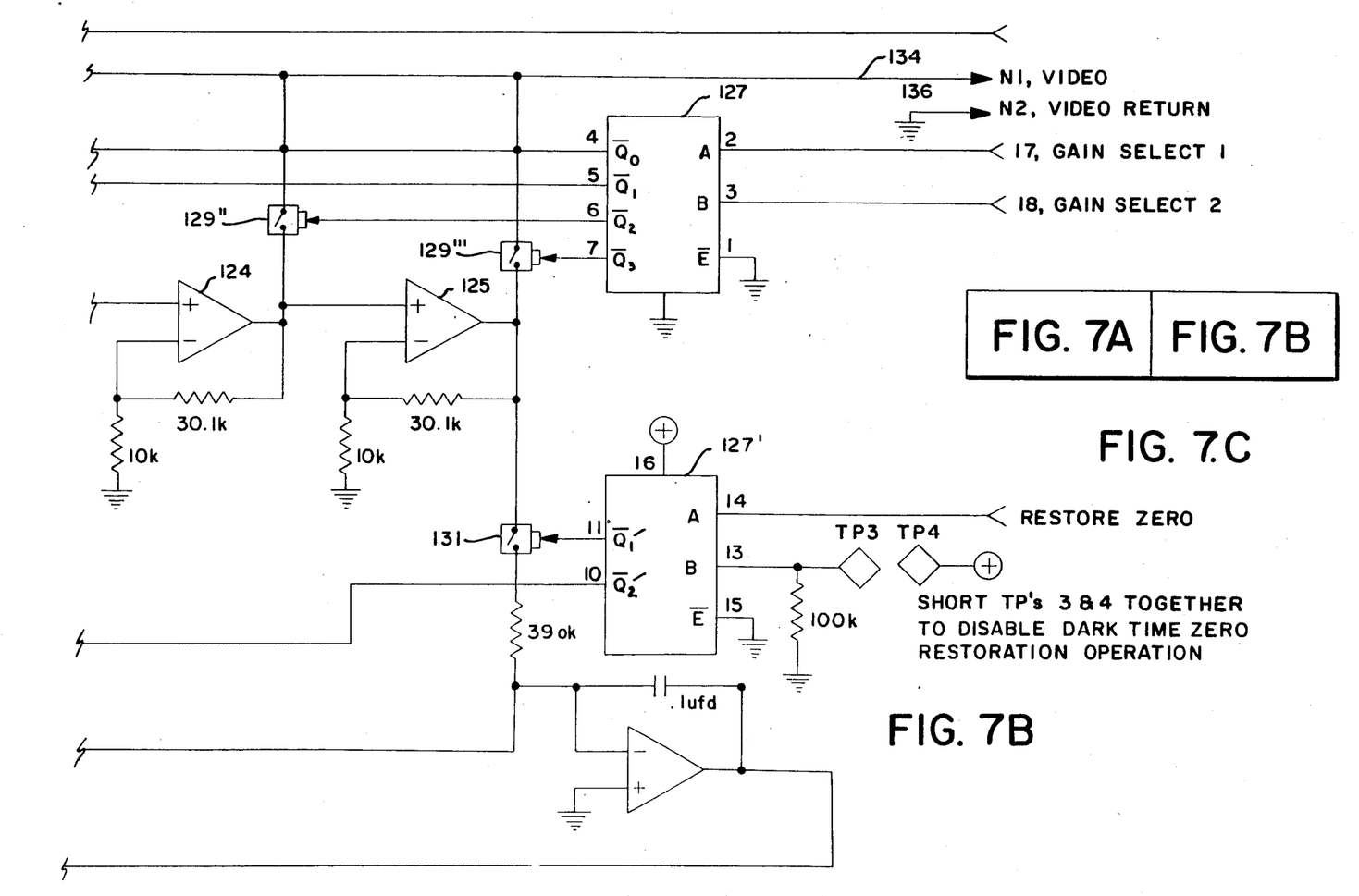
FIG. 7B is the remaining portion of the detailed schematic for the pre-amplifier electronic circuitry shown in FIG. 7A.

FIGS. 7A and 7B present the detailed circuitry for the pre-amplifiers 64 and 66. The circuit component values for the resistors and capacitors are shown accompanying the individual components. The circuitry for both pre-amplifiers is identical and thus FIGS. 7A and 7B represent both pre-amplifier circuits. The other components shown in these figures are identified in Table 1.

In operation the signal from photodiode 60 (or 62 depending upon which preamplifier is being considered) is initially amplified by differential amplifiers 118 and 119 and their associated resistors and capacitors. The output from amplifier 119 is then directed to a series of differential amplifiers 121, 122, 123, 124, and 125 with the particular gain factor selected by gain selector signal 1 or gain selector signal 2, (line 17 or 18 (FIG. 7B) in conjunction with the output from decoders 127 and 127' whose outputs (Q0, Q1, Q2, Q3, for decoder 127 and Q1', Q2', for decoder 127') respectively control the operation of gates 129, 129', 129'', 129''', 131 and 131'. Output 134 is then presented to the algebraic comparison circuitry 68.

Figure 7D:
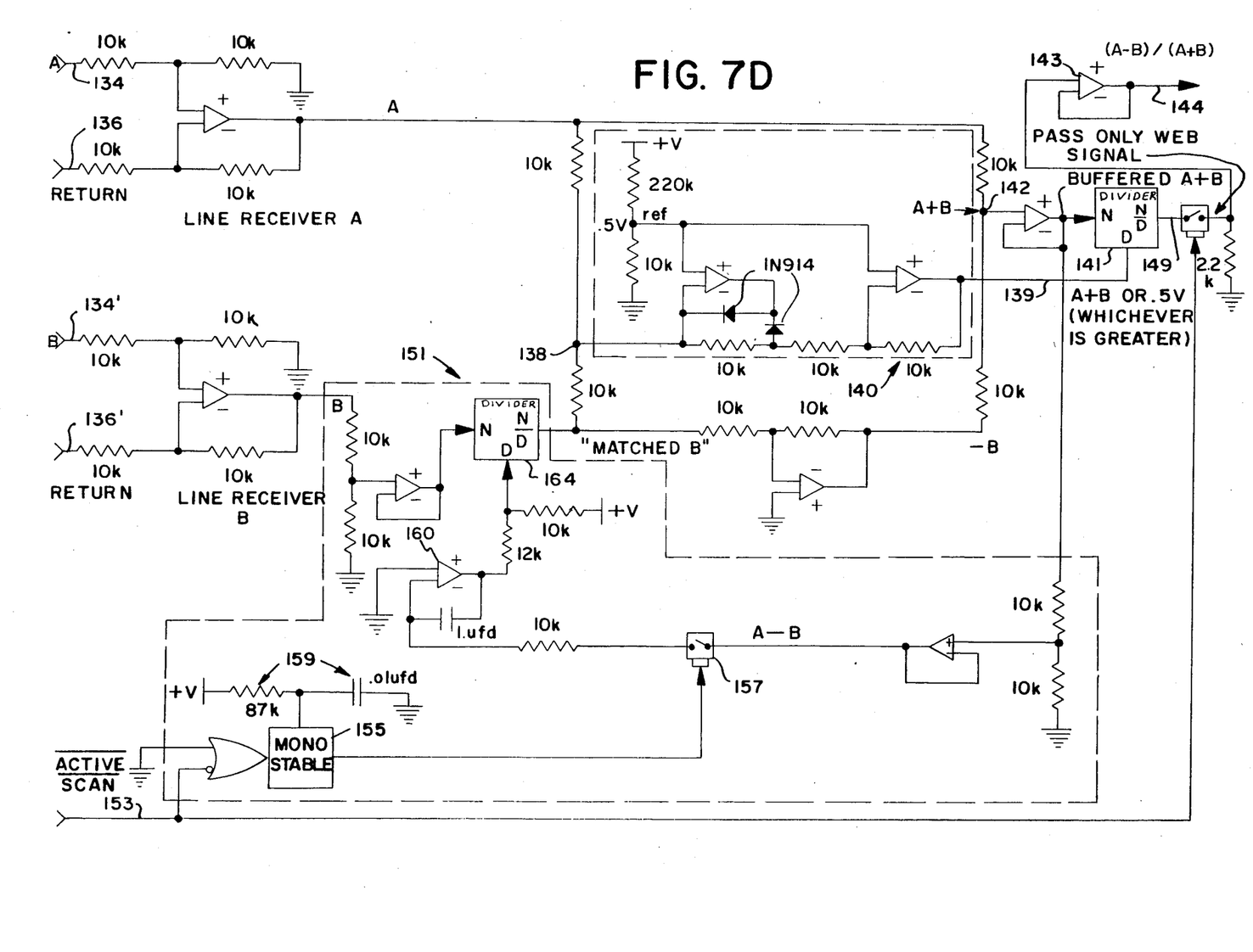
FIG. 7D is a detailed schematic of the algebraic comparison circuitry forming part of the present invention.

FIG. 7D shows the algebraic comparison circuitry in detail. The components shown in FIG. 7D are identified in Table 2.

TABLE 1

| REFERENCE NO. | DESCRIPTION | COMPONENT |
|---|---|---|
| 118,119, 121-125 | Differential Amplifier | TL084 Texas Instruments Dallas, TX |
| 127, 127' | Decoder | MC14556B Motorola Chicago, IL |
| 129, 129' 129'', 129''', 131, 131', 131'', 131''' | Electronic Switch | HI201 Harris Semiconductor Melbourne, FL |

TABLE 2

| REFERENCE NO. | DESCRIPTION | COMPONENT |
|---|---|---|
| 143 | Differential Amplifier | *TL084 Texas Instruments Dallas, TX |
| 155 | Monostable Multivibrator | |
| 157 | Electronic Switch | *HI201 Harris Semiconductor Melbourne, FL |
| 164 | Analog Divider | *DIV100 Burr-Brown Tucson, AZ |

*All other similar components shown in FIG. 7D use the same part.

The circuitry basically takes the input from receiver A (output line 134') and adds it to the value of receiver B (output line 134'). This addition occurs at node 138. In order to insure that this value does not become arbitrarily small (such as if both A and B have very low voltages) a clamping circuit 140 is used to insure that the value of A+B does not become smaller than 0.5 volts. If it does, output line 139 is clamped to 0.5 volts and becomes the divisor input for divider 141.

Subtraction of signal B from signal A occurs at node 142. This signal is buffered by amplifier 145 and then presented to the numerator input of divider 141. The divider+output 149 represents the value of (A-B)/(A+B) which is passed to amplifier 143 for buffering. The amplifier's output 144, as shown in FIG. 7E is then presented to bandpass filter 146 of processing circuitry 72.

Circuit 151 insures that the value of B equals the value of A when no defect is sensed. In order to achieve this result, an active scan signal 153 is used to indicate when a new scan is to occur. This signal may be a web edge detection or it can be timed to begin at a particular instant in the movement of scanning mirror 40. In any event, signal 153 triggers monostable multivibrator 155 which in turn triggers gate 157. Multivibrator 155 enables gate 157 for approximately 10% of the flying spot scan through use of RC time delay circuit 159.

The input to gate 157 is the buffered value of (A−B). This signal is presented to the negative input of differential amplifier 160. The output of this amplifier is clamped positive by the input to resistor 162 and then presented to the denominator input of divider 164. The numerator input to this divider is signal B divided by two.

Thus during the first 10% of each scan the value of signal B is adjusted upward or downward by the feedback of signal (A+B) so that the value of B is the same as the value of A when no defect is sensed. In this way variations in the gain of pre-amplifiers 64 and 66 as well as of photodetectors 60 and 62 are automatically compensated. Since the normalization of signal B to signal A occurs at the beginning of each scan, small errors which may result from a defect being present on any one scan are automatically compensated for on subsequent scans.

Although other algebraic manipulations of the two amplifier signals can be used, such as straight division (A/B), it is found that the use of the algebraic manipulation (A−B)/(A+B) is more linear especially when the absolute changes of signals A and B are large.

FIG. 7E shows that processor circuitry 72 typically includes a bandpass filter 146 comprising a low-pass filter 147 and a high-pass filter 148 whose output 150 is presented to a comparator 152. There the signal is compared to a threshold voltage representing the amplitude of a signal which, if exceeded, indicates the presence of a defect. The output of the comparator 154 can then be used to activate circuitry such as relays, counters or a display such as on console 26 (see FIG. 1). Of course more than one comparator representing different types of defect threshold levels can be used for identifying various types of defects such as holes, streaks, dark spots and the like.

In addition to comparing the output voltage from the bandpass filter to a threshold voltage, integration of the bandpass filter can also be used to help characterize the appearance and type of the defect encountered. This is shown schematically in FIG. 7E by integrator 156 having an output 158. Other processing techniques including consecutive scan analysis for identifying defects can be used. The present flying spot scanner system is not intended to be limited to any particular type of processing circuitry.

Thus what has been described is an adjacent flying spot scanner system that uses a split beam technique for determining the presence of defects. Algebraic comparison of separate footprint output is used to allow identification of defect types. The system operates in the spacial domain and thus does not use time differentiation.

Through this technique and with the use of differently shaped mirrored surfaces, the sensitivity of the system to different types of defects can be maximized. Although the preferred embodiment shows the use of two mirrored surfaces and two adjacent flying spots, more than two adjacent flying spots could be utilized.

Thus the objects set forth above and those made apparent from the preceding description are efficiently attained and, since certain changes may be made in carrying out the above construction and method without departing from the scope of the invention, it is intended that all matter contained in the above description or shown in the accompanying drawings shall be interpreted as illustrative and not in a limiting sense.

It is also to be understood that the following claims are intended to cover all the generic and specific features of the invention herein described and all statements of the scope of the invention, which as a matter of language, might be said to fall therebetween.

Having described the invention, what is claimed is:

1. A flying spot scanner system for use with a web moving along a path, comprising:
   (A) means for repetitively scanning the moving web;
   (B) means for establishing at least two adjacent flying spots on the moving web the flying spots periodically traversing the web by the scanning means;
   (C) means for separately sensing the amount of radiation received from each flying spot, with each of the sensing means generating a separate signal;
   (D) means for algebraically combining the signals produced by each sensing means; and
   (E) means for comparing the algebraically combined signal with at least one threshold value indicative of a particular type of defect, so as to produce an output signal if the algebraically combined signal is greater than the threshold value;
   whereby the special algebraic difference in the radiation received from the adjacent flying spots is indicative of the presence or absence of a particular defect type by comparison to a threshold value, 2. A flying spot scanner system as defined in claim 1 wherein the means for establishing adjacent flying spot images comprises a primary focusing lens in combination with a split beam mirror, the split beam mirror having at least two adjacent mirrored surfaces, each mirrored surface having a shape proportional to the shape of one of the flying spot shapes.

3. A flying spot scanner system as defined in claim 1 or 2 wherein the algebraic combining means electronically combines two flying spot sensing signals in the following manner, (A−B)/(A+B); where A and B each represent the magnitude of one of the sensing signals.

4. A flying spot scanner system as defined in claim 3 further wherein the algebraic combining means limits the minimum value of the numerator, (A+B), to a predetermined value.

5. A flying spot scanner system as defined in claim: 4 further comprising means for generating a scan signal representing the start of each scan by the web scanning means, and also comprising means responsive to the can signal for normalizing the value of one sensing signal to another sensing signal during part of each scan.

6. A flying spot scanner system as defined in claim 5 wherein the means for separately sensing the amount of radiation from each flying spot includes a secondary lens for each flying spot image and a photodetector positioned at the approximate focal point of each secondary lens.

7. A flying spot scanner system as defined in claim 1 wherein the means for separately sensing the amount of radiation from each flying spot includes a secondary lens for each flying spot image and a photodetector positioned at the approximate focal point of each secondary lens.

8. A flying spot scanner system as defined in claim 1 or 2 further comprising means for generating a scan signal representing the start of each scan by the web scanning means, and also comprising means responsive to the scan signal for normalizing the value of one sensing signal to another sensing signal during part of each scan so as to obtain greater accuracy for the algebraic combinging.

9. A flying spot scanner system as defined in claim 2 wherein the mirrored surfaces of the split beam mirror each have a generally triangular shape with the base of each triangle adjacent to one another.

10. A flying spot scanner system as defined in claim 2 wherein the mirrored surfaces of the split beam mirror have a rectangular shape with the edge of one mirror surface adjacent that of the other mirror surface.

11. A flying spot scanner system as defined in claim 1 or 2, further comprising an illumination source for back lighting the web along an illumination area and wherein the web scanning means comprise means for traversing the web along a path within the illumination area.

12. A flying spot scanner system for use with a web movable along a path, comprising:
  (A) at least two radiation detectors;
  (B) means for traversely scanning across the moving web so as to establish a flying spot path for at least an adjoining pair of flying spots;
  (C) means to radiate the web as it passes through the region traversely scanned by the scanning means;
  (D) means for individually transferring to each radiation detector an image of one of the flying spots;
  (E) means for electronically algebraically comparing the outputs from the individual radiation detectors so as to establish a single output representing such algebraic comparison; and
  (F) means for comparing the algebriacally combined signal with at least one threshold value indicative of a defect, so as to produce an output signal if the algebraically combined signal is greater than the threshold value;

whereby the special algebraic difference in the radiation received from the adjacent flying spots is indicative of the presence or absence of a defect by comparison to a threshold value.

13. A flying spot scanner system as defined in claim 12 wherein the radiation detectors comprise photodiodes.

14. A flying spot scanner system as defined in claim 13 wherein the scanning means comprises a mirror for oscillating between two points a taut wire upon which the mirror is mounted, and an oscillator circuit for imparting vibrational motion to the taut wire.

15. a flying spot scanner system as defined in claim 14 wherein the means to radiate the scanning path of the web comprises a light box which is positioned beneath the web with respect to the scanning means.

16. A flying spot scanner system as defined in claim 15 wherein the means to transfer individual images of the flying spots to the radiation detectors comprises at least a double faceted mirror positioned within the optical path of the scanning means so as to separate the individual image.

17. A flying spot scanner system as defined in claim 12, 13, 14, or 15, in which two radiation detectors are used in combination with two flying spots and wherein the means to transmit individual images to radiation detectors comprises a mirror with two mirrored surfaces in the optical path of the scanning means so as to project one flying spot individually with respect to one radiation detector.

18. A flying spot scanner system as defined in claim 12 wherein the means for establishing an adjoining pair of flying spots comprises a primary focusing lens in combination with a split beam mirror.

19. A flying spot scanning system as defined in claim 18 wherein the flying spot shape for each flying spot is generally triangular shaped and wherein the shape is generated by a corresponding generally triangular mirrored surface on the split beam mirror with the base of each mirrored surface adjacent that of the other mirrored surface.

20. A flying spot scanner system as defined in claim 18 wherein the flying spot shape for each flying spot is of a rectangular shape and wherein the shape is generated by a corresponding generally rectangular mirrored surface on the split beam mirror.

21. A flying spot scanner system as defined in claim 19 or 20 wherein the means for individually transferring to each radiation detector an image of one of the flying spots includes a secondary lens and a photodetector for each flying spot, each secondary lens positioned to focus one flying spot image onto one photodetector.

22. A flying spot scanner system as defined in claim 1 wherein the adjacent flying spots each have a generally triangular shape and wherein the algebraic combining means electronically comgines two flying spot sensing signals in the following manner, $(A-B)/(A+B)$; where A and B each represent the magnitude of one of the sensing signals; and further wherein said algebraically combined signal generates a unique output waveform for different type surface defects, including small holes, small spots, and streaks.

23. A flying spot scanner system as defined in claim 22 further comprising means for generating a scan signal representing the start of each scan by the web scanning means, and also comprises means responsive to the scan signal for adjusting the magnitude of signal B with respect to signal A so that the value of B is the same as the value of A when no defect is sensed, wherein this adjustment of the value of B with respect to the value of A occurs within the first 10% of each scan as initiated by the scan starting signal.

24. A flying spot scanner system as defined in claim 1 wherein the adjacent flying spots each have a generally rectangular shape and wherein the algebraic combining means electronically combines two flying spot sensing signals in the following manner, $(A-B)/(A+B)$; where A and B each represent the magnitude of one of the sensing signals; and further wherein said algebraically combined signal generates a unique output waveform for different types of surface defects, including small holes, small spots, and streaks.

25. A flying spot scanner system as defined in claim 24 further comprising means for generating a scan signal representing the start of each scan by the web scanning means, and also comprises means responsive to the scan signal for adjusting the magnitude of signal B with respect to signal A to so that the value of B is the same as the value of A when no defect is sensed, wherein this adjustment of the value of B with respect to the value of A occurs within the first 10% of each scan as initiated by the scan starting signal.

26. A flying spot scanner system as defined in claim 12 wherein the adjacent flying spots each have a generally triangular shape and wherein the albebraic combining means electronically combines two flying spot sensing signals in the following manner, $(A-B)/(A+B)$; where A and B each represent the magnitude of one of the sensing signals; and further wherein said algebraically combined signal generates a unique output waveform for different types of surface defects, including small holes, small spots, and streaks, 27. A flying spot scanner system as defined in claim 26 further comprising means for generating a scan signal representing the start of each scan by the web scanning means, and also comprises means responsive to the scan signal for adjusting the magnitude of signal B with respect to signal A so that the value of B is the same as the value of A when no defect is sensed, wherein this adjustment of the value of B with respect to the value of A occurs within the first 10% of each scan as initiated by the scan starting signal.

28. A flying spot scanner system as defined in claim 12 wherein the adjacent flying spots each have a generally rectangular shape and wherein the algebraic combining means electronically combines two flying spot sensing signals in the following manner, $(A-B)/(A+B)$; where A and B each represent the magnitude or one of the sensing signals; and further wherein said algebraically combined signal generates a unique output waveform for different types of surface defects, including small holes, small spots, and streaks.

29. Flying spot scanner system as defined in claim 28 further comprising means for generating a scan signal representing the start of each scan by the web scanning means, and also comprises means responsive to the scan signal for adjusting the magnitude of signal B with respect to signal A so that the value of B is the same as the value of A when no defect is sensed, wherein this adjustment of the value of B with respect to the value of A occurs within the first 10% of each scan as initiated by the scan starting signal.

30. A flying spot scanner system as defined in claim 3 further comprising means for generating a scan signal representing the start of each scan by the web scanning means, and also comprises means responsive to the scan signal for adjusting the magnitude of signal B with respect to signal A so that the value of B is the same as the value of A when no defect is sensed, wherein this adjustment of the value of B with respect to the value of A occurs within the first 10% of each scan as initiated by the scan starting signal.

* * * * *